(12) United States Patent
Voeste et al.

(10) Patent No.: US 8,722,577 B2
(45) Date of Patent: May 13, 2014

(54) PLANT HEALTH COMPOSITION

(75) Inventors: Dirk Voeste, Limburgerhof (DE); Egon Haden, Kleinniedesheim (DE); Marco-Antonio Tavares-Rodrigues, Sao Paulo (BR); Edson Begliomini, Sao Paulo (BR)

(73) Assignee: BASF SE, Ludwigshafen (DE)

( * ) Notice: Subject to any disclaimer, the term of this patent is extended or adjusted under 35 U.S.C. 154(b) by 609 days.

(21) Appl. No.: 12/524,137

(22) PCT Filed: Feb. 5, 2008

(86) PCT No.: PCT/EP2008/051395
§ 371 (c)(1),
(2), (4) Date: Jul. 22, 2009

(87) PCT Pub. No.: WO2008/095926
PCT Pub. Date: Aug. 14, 2008

(65) Prior Publication Data
US 2010/0105669 A1      Apr. 29, 2010

(30) Foreign Application Priority Data
Feb. 6, 2007 (EP) .................... 07101847

(51) Int. Cl.
*A01N 47/02* (2006.01)
*A01N 37/44* (2006.01)
*A01N 37/46* (2006.01)
*A01N 47/24* (2006.01)

(52) U.S. Cl.
USPC ............ 504/100; 514/403; 514/406; 514/407

(58) Field of Classification Search
USPC .................. 514/383, 403, 406, 407; 504/100
See application file for complete search history.

(56) References Cited

U.S. PATENT DOCUMENTS

| 5,707,934 A | 1/1998 | Royalty et al. |
| 6,245,792 B1 * | 6/2001 | Muller et al. ................. 514/383 |
| 2005/0032903 A1 | 2/2005 | Suarez-Cervieri et al. |
| 2007/0093389 A1 | 4/2007 | Rademacher et al. |

FOREIGN PATENT DOCUMENTS

| FR | 2 773 155 A1 | 7/1999 |
| WO | WO 01/26468 A2 | 4/2001 |
| WO | WO-2005/058040 A1 | 6/2005 |
| WO | WO-2006/023899 A1 | 3/2006 |
| WO | WO-2006/069654 A2 | 7/2006 |
| WO | WO-2006/089876 A1 | 8/2006 |

OTHER PUBLICATIONS

Jabs, T. et al., "Anti-oxidative and anti-senescence effects of the strobilurin pyraclostrobin in plants . . . " BCPC Conference Pests & Diseases, vol. 2, pp. 941-946 (2002).*
HCAPLUS abstract 2002:602334 (2002).*
CABA abstract 1993:16591 (1993).*
Meier, U. (ed.), Growth stages of mono- and dicotyledonous plants, BBCH Monograph, Federal Biological Research Centre for Agriculture and Forestry, pp. 1-158.*
The barley growth guide, HGCA, 2005, pp. 1-28.*
Bartlett et al., "Review the strobilurin fungicides", Pest Management Science 2002, 58, pp. 649-662.
Fletcher et al., "Triazoles as Plant Growth Regulators and Stress Protectants", Horticultural Reviews 2000, 24, pp. 58.
Sconyers et al., "Asian Soybeans Rust Development in 2005: A Perspective from the Southeastern United States", APSnet Feature, Jan. 2006, pp. 1-20.

* cited by examiner

*Primary Examiner* — John Pak
(74) *Attorney, Agent, or Firm* — Birch, Stewart, Kolasch & Birch, LLP

(57) ABSTRACT

The present invention relates to a composition containing (A) at least one specific carbamate fungicide, (B) at least one specific insecticide and optionally (C) at least one azole, the use of this composition for improving plant health and a method for improving plant health by treating a plant, its propagules or the locus where the plant is growing or is to grow with the above composition.

5 Claims, No Drawings

PLANT HEALTH COMPOSITION

The present invention relates to a composition containing (A) at least one specific carbamate fungicide, (B) at least one specific insecticide and optionally (C) at least one azole, the use of this composition for improving plant health and a method for improving plant health by treating a plant, its propagules or the locus where the plant is growing or is to grow with the above composition.

In crop protection, there is a continuous need for compositions that improve the health of plants. Healthier plants are desirable since they result among other in better crop yields and/or a better quality of the plants or crops. Healthier plants also better resist to biotic and/or abiotic stress. A better resistance to biotic stress in turn allows reducing the quantity of pesticides, which also helps avoiding the development of resistances against the respective pesticides.

It was therefore an object of the present invention to provide a pesticidal composition which solves the problems outlined above. In particular, the composition should improve plant health.

We have found that this object is achieved by a composition comprising a specific carbamate fungicide and a specific insecticide. Accordingly, in one aspect, the present invention relates to the use of a composition comprising
(A) at least one compound of formula I

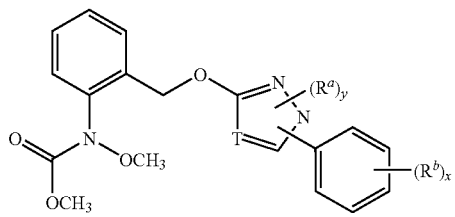

where
T is CH or N;
$R^a$ and $R^b$ are independently of each other halogen, $C_1$-$C_4$-alkyl or $C_1$-$C_4$-haloalkyl;
x is 0, 1 or 2; and
y is 0 or 1;
or the agriculturally acceptable salts thereof;
and
(B) at least one insecticide selected from GABA-antagonists and nicotonic receptor agonists/antagonists
for improving the plant health of at least one plant variety.

In the terms of the present invention "composition" is not restricted to a physical mixture containing components (A) and (B) (and optionally component (C), see below), but refers to any preparation form of components (A) and (B) (and optionally (C)), the use of which is time- and locus-related. In one embodiment of the invention "composition" refers to a physical mixture of the at least one component (A) (=at least one compound I) and the at least one component (B) (=at least one of the specific insecticides). In another embodiment of the invention, "composition" refers to the components (A) and (B) (and optionally (C)) being formulated separately but applied to the plant, the propagule from which it is to grow and/or the locus in which it grows or is to grow in a temporal relationship, i.e. simultaneously or subsequently, the subsequent application having a time interval which allows a combined action of the two components. For instance, in one preferred embodiment, one of the components (which is preferably component (B)) is applied to the propagules from which the plant (i.e. the plant the health of which is to be improved) is to grow or to the locus wherein the propagules are to be planted (i.e. the growing medium) and the other component (which is preferably component (A), optionally together with component (C)) is applied to the plant or parts thereof after its emergence.

One example for a composition wherein component (A) and component (B) are formulated separately is a two-component-kit. Accordingly, in the terms of the present invention, "composition" can also refer to the use of a two-component-kit comprising a first component which contains the at least one compound I, a liquid or solid carrier and optionally at least one surface-active compound and/or at least one conventional auxiliary and a second component which contains the at least one insecticide selected from GABA-antagonists and nicotinic receptor agonists/antagonists, a liquid or solid carrier and optionally at least one surface-active compound and/or at least one conventional auxiliary. Suitable liquid and solid carriers, surface-active compounds and auxiliaries are described below.

One example for a composition wherein component (A) and component (B) are formulated separately and which further contains component (C) is a three-component-kit formulated in two parts. In this case, the third component (C) is formulated together with either component (A) or (B) and preferably with component (A). Accordingly, in the terms of the present invention, "composition" can also refer to the use of a three-component-kit formulated in two parts, comprising a first part which contains the at least one compound I (component (A)), the at least one azole fungicide (component (C)), a liquid or solid carrier and optionally at least one surface-active compound and/or at least one conventional auxiliary and a second part which contains the at least one insecticide selected from GABA-antagonists and nicotinic receptor agonists/antagonists (component (B)), a liquid or solid carrier and optionally at least one surface-active compound and/or at least one conventional auxiliary. Suitable liquid and solid carriers, surface-active compounds and auxiliaries are described below.

The organic moieties mentioned in the above definitions of the variables are—like the term halogen—collective terms for individual listings of the individual group members. The prefix $C_n$-$C_m$ indicates in each case the possible number of carbon atoms in the group.

Halogen will be taken to mean fluoro, chloro, bromo and iodo, preferably fluoro, chloro, and bromo and in particular fluoro and chloro.

$C_1$-$C_4$-alkyl is a linear or branched alkyl group having 1 to 4 carbon atoms. Examples are methyl, ethyl, propyl, isopropyl, n-butyl, sec-butyl, isobutyl and tert-butyl.

$C_1$-$C_4$-haloalkyl is a linear or branched alkyl group having 1 to 4 carbon atoms, as defined above, wherein at least one hydrogen atom is replaced by a halogen atom. Examples are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The below remarks as to preferred embodiments of components (A) and (B) and the optional component (C), to their preferred use and methods of using them are to be understood either each on their own or preferably in combination with each other.

Owing to the basic nitrogen atoms in the azole moieties, the compounds of the formulae I, the azole fungicides of the optional component (C) and also several compounds selected from the insecticides of component (B) (for example compounds II and III described below) are capable of forming salts or adducts with inorganic or organic aids or with metal ions. They can be formed in a customary method, e.g. by reacting the compounds with an acid of the anion in question.

Suitable agriculturally useful salts are especially the salts of those cations or the acid addition salts of those acids the cations and anions of which do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formiate, acetate, propionate and butyrate. They can be formed by reacting the compounds of the formulae I or II or III (as to compounds II and III see below) with an acid of the corresponding anion, preferably of hydrochloric acid, hydrobromic acid, sulfuric acid, phosphoric acid or nitric acid.

In compound I, $R^a$ is preferably $C_1$-$C_4$-alkyl, in particular methyl.

$R^b$ is preferably halogen, in particular Cl, $C_1$-$C_4$-alkyl, in particular methyl, or $C_1$-$C_4$-haloalkyl, in particular $CF_3$.

Preferred compounds I are compiled in following table.

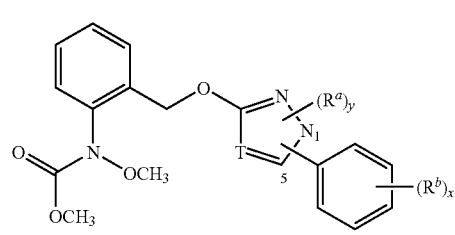

(I)

| Comp. No. | T | $(R^a)_y$ | Position of the group phenyl-$(R^b)_x$ | $(R^b)_x$ |
|---|---|---|---|---|
| I-1 | N | — | 1 | 2-F |
| I-2 | N | — | 1 | 3-F |
| I-3 | N | — | 1 | 4-F |
| I-4 | N | — | 1 | 2-Cl |
| I-5 | N | — | 1 | 3-Cl |

-continued

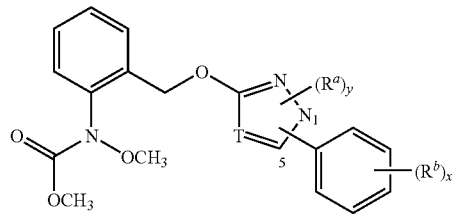

(I)

| Comp. No. | T | $(R^a)_y$ | Position of the group phenyl-$(R^b)_x$ | $(R^b)_x$ |
|---|---|---|---|---|
| I-6 | N | — | 1 | 4-Cl |
| I-7 | N | — | 1 | 2-Br |
| I-8 | N | — | 1 | 3-Br |
| I-9 | N | — | 1 | 4-Br |
| I-10 | N | — | 1 | 2-$CH_3$ |
| I-11 | N | — | 1 | 3-$CH_3$ |
| I-12 | N | — | 1 | 4-$CH_3$ |
| I-13 | N | — | 1 | 2-$CH_2CH_3$ |
| I-14 | N | — | 1 | 3-$CH_2CH_3$ |
| I-15 | N | — | 1 | 4-$CH_2CH_3$ |
| I-16 | N | — | 1 | 2-$CH(CH_3)_2$ |
| I-17 | N | — | 1 | 3-$CH(CH_3)_2$ |
| I-18 | N | — | 1 | 4-$CH(CH_3)_2$ |
| I-19 | N | — | 1 | 2-$CF_3$ |
| I-20 | N | — | 1 | 3-$CF_3$ |
| I-21 | N | — | 1 | 4-$CF_3$ |
| I-22 | N | — | 1 | 2,4-$F_2$ |
| I-23 | N | — | 1 | 2,4-$Cl_2$ |
| I-24 | N | — | 1 | 3,4-$Cl_2$ |
| I-25 | N | — | 1 | 2-Cl, 4-$CH_3$ |
| I-26 | N | — | 1 | 3-Cl, 4-$CH_3$ |
| I-27 | CH | — | 1 | 2-F |
| I-28 | CH | — | 1 | 3-F |
| I-29 | CH | — | 1 | 4-F |
| I-30 | CH | — | 1 | 2-Cl |
| I-31 | CH | — | 1 | 3-Cl |
| I-32 | CH | — | 1 | 4-Cl |
| I-33 | CH | — | 1 | 2-Br |
| I-34 | CH | — | 1 | 3-Br |
| I-35 | CH | — | 1 | 4-Br |
| I-36 | CH | — | 1 | 2-$CH_3$ |
| I-37 | CH | — | 1 | 3-$CH_3$ |
| I-38 | CH | — | 1 | 4-$CH_3$ |
| I-39 | CH | — | 1 | 2-$CH_2CH_3$ |
| I-40 | CH | — | 1 | 3-$CH_2CH_3$ |
| I-41 | CH | — | 1 | 4-$CH_2CH_3$ |
| I-42 | CH | — | 1 | 2-$CH(CH_3)_2$ |
| I-43 | CH | — | 1 | 3-$CH(CH_3)_2$ |
| I-44 | CH | — | 1 | 4-$CH(CH_3)_2$ |
| I-45 | CH | — | 1 | 2-$CF_3$ |
| I-46 | CH | — | 1 | 3-$CF_3$ |
| I-47 | CH | — | 1 | 4-$CF_3$ |
| I-48 | CH | — | 1 | 2,4-$F_2$ |
| I-49 | CH | — | 1 | 2,4-$Cl_2$ |
| I-50 | CH | — | 1 | 3,4-$Cl_2$ |
| I-51 | CH | — | 1 | 2-Cl, 4-$CH_3$ |
| I-52 | CH | — | 1 | 3-Cl, 4-$CH_3$ |
| I-53 | CH | — | 1 | — |
| I-55 | CH | 5-$CH_3$ | 1 | 3-$CF_3$ |
| I-56 | CH | 1-$CH_3$ | 5 | 3-$CF_3$ |
| I-57 | CH | 1-$CH_3$ | 5 | 4-Cl |
| I-58 | CH | 1-$CH_3$ | 5 | — |

In more preferred compounds, T is CH.
In more preferred compounds, y is 0.
In more preferred compounds, x is 0 or 1. Specifically, x is 1.

Particularly preferred compounds I are compounds I-12, I-23, I-32 and I-38. Even more preferred is compound I-32, which is also known under the common name of pyraclostrobin.

Compounds of formula I and methods for producing them are generally known. For instance, compounds I-1 to I-55 and methods for producing them are described in WO 96/01256 and EP-A-0804421 and compounds I-56 to I-58 and their preparation are described in WO 99/33812, the contents of which are hereby fully incorporated by reference. Further compounds I can be prepared by methods analogous to those described in the above references. Compounds I are commonly known as fungicides.

The GABA-antagonists of component (B) are preferably selected from acetoprole, endosulfan, vaniliprole, pyrafluprole, pyriprole, the phenylpyrazole compound of the formula

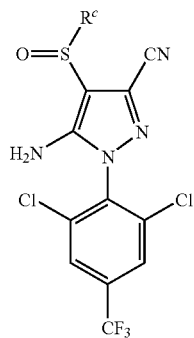

(II)

where each $R^c$ independently is $C_1$-$C_4$-alkyl or $C_1$-$C_4$-haloalkyl;
or an agriculturally acceptable salt thereof; and the phenylpyrazole compound of the formula III

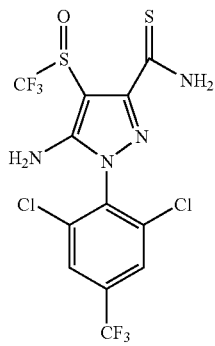

(III)

or an agriculturally acceptable salt thereof.

Preferably, the GABA antagonists are selected from compounds of formula II.

In compounds II, $R^c$ is preferably ethyl or trifluoromethyl. The compound where $R^c$ is ethyl is also known under the common name ethiprole and the compound where $R^c$ is trifluoromethyl is known under the common name fipronil. More preferably, $R^c$ is trifluoromethyl.

The nicotinic receptor agonists/antagonists of component (B) are preferably selected from acetamiprid, clothianidin, dinotefuran, imidacloprid, nitenpyram, thiacloprid and thiamethoxam, more preferably from acetamiprid, clothianidin, imidacloprid and thiamethoxam and in particular from imidacloprid and thiamethoxam.

GABA antagonists, nicotinic receptor agonists/antagonists and methods for producing them are generally known. For instance, the commercially available compounds may be found in The Pesticide Manual, 13th Edition, British Crop Protection Council (2003) among other publications.

Preferably, the insecticide of component (B) is selected from GABA antagonists. Reference is made to the above-mentioned preferred embodiments of the GABA antagonists. In particular, the insecticide of component (B) is fipronil.

In a specific embodiment of the invention, the composition to be used according to the invention additionally contains (C) at least one azole fungicide.

Azole fungicides, which are also referred to as conazole fungicides, are fungicidally active compounds which comprise an aromatic 5-membered nitrogen heterocycle and in particular an imidazole ring ("imidazole conazole" or a triazole ring "triazole conazole". Azole fungicides are, in principle, known to the skilled worker and described for example in Farm Chemicals Handbook, Meister Publishing Company or in the Compendium of Pesticide Common Names, http://www.hclrss.demon.co.uk/, which are herewith referred to in their entirety.

Preferred azole fungicides are those which are known under the common names bitertanol, bromoconazole, cyproconazole, difenoconazole, dinitroconazole, epoxiconazole, fenbuconazole, fluquiconazole, flusilazol, flutriafol, hexaconazole, imazalil, metconazole, myclobutanil, penconazole, propiconazole, prochloraz, prothioconazole, tebuconazole, triadimefon, triadimenol, triflumizol and triticonazole. Especially preferred is epoxiconazole.

The composition used according to the invention can be a binary composition or a ternary or an even higher composition. Binary compositions are understood to contain one component (A), i.e. one compound I, and one component (B), i.e. one of the specific insecticides, e.g. one compound II. Ternary compositions are understood to contain one component (A)), i.e. one compound I, and two different components (B), i.e. two of the specific insecticides, e.g. two compounds II, or one component (B), i.e. one of the specific insecticides, e.g. one compound II, and two different components (A), i.e. two compounds I, the first variant being preferred, or are understood to contain one component (A), i.e. one compound I, one component (B), i.e. one of the specific insecticides, e.g. one compound II, and one component (C), i.e. one azole fungicide.

Preferably, the composition used according to the invention comprises one compound of formula I, specifically pyraclostrobin, and one of the specific insecticides of component (B), in particular one compound II, specifically fipronil. Alternatively, the composition used according to the invention preferably comprises one compound of formula I, specifically pyraclostrobin, one of the specific insecticides of component (B), in particular one compound II—specifically fipronil—, thiamethoxam or imidacloprid and more specifically fipronil, and one azole fungicide, specifically epoxiconazole.

As already explained above, the term "the composition of the invention comprises/contains" does not restrict the composition to a physical mixture, but refers to the application of the components to the plant/the propagules from which the plant is to grow/the locus where the plant is to grow or growing in a local and time context.

In the compositions used according to the invention, components (A) and (B) are employed in amounts to afford a synergistic effect. The weight ratio of the component (A) to the component (B) is preferably from 200:1 to 1:200, more preferably from 100:1 to 1:100, more preferably from 50:1 to 1:50 and in particular from 10:1 to 1:10. The weight ratio refers to the total weight of compounds I and the specific insecticides, e.g. compounds II, contained in component (A) and (B) of the composition.

If the composition used according to the invention contains the component (C), the weight ratio of the component (A) to the component (C) is preferably from 200:1 to 1:200, more preferably from 100:1 to 1:100, more preferably from 50:1 to 1:50, even more preferably from 10:1 to 1:10, in particular from 10:1 to 1:1 specifically from 5:1 to 1:1 and more specifically from 3:1 to 2:1. The weight ratio refers to the total weight of compounds I and the azole fungicides contained in component (A) and (C) of the composition.

The compositions are used for improving the health of plants when applied to plants, parts of plants, propagules of the plants or to their actual or intended locus of growth.

Thus, the invention also relates to a method for improving the health of plants, which comprises treating the plant, a part of the plant, the locus where the plant is growing or is expected to grow, and/or the propagules from which the plant grows with the composition used according to the invention. According to this inventive method, the plant, the locus where the plant is growing or is expected to grow, and/or the propagules from which the plant grows are treated simultaneously (together or separately) or—preferably—subsequently with the components (A) and (B). Of course, the subsequent application is carried out with a time interval which allows a combined action of the two components. Preferably, the time interval for a subsequent application of components (A) and (B) ranges from a few seconds up to several months, preferably from a few seconds up to 12 month, more preferably from a few seconds up to 10 months, in particular from 1 week up to 10 months, more particularly from 1 month to 10 months and specifically from 1 month to 8 months. As a rule, the time interval depends on the plant species the plant health of which is to be improved. For instance, if the plant is a spring crop, i.e. an annual plant which is sown/planted in spring, the time interval is preferably in the range of from 1 to 5 months and specifically from 3 to 4 months. If the plant is a winter crop, i.e. an annual plant which is sown/planted in autumn or early winter, the time interval is preferably in the range of from 4 to 10 months and specifically from 5 to 8 months.

If component (C) is contained in the composition used according to the invention, it is preferably applied simultaneously or within a very short time interval (such as from a few seconds up to 1 day) with one of components (A) and (B) and preferably (A).

In a preferred embodiment, the propagules from which the plant (i.e. the plant the health of which is to be improved) is to grow are treated with component (B). After emergence, i.e. after the young plant has broken through the surface of the growing medium, the plant or parts of the plant are then treated once or several times with component (A) and optionally with component (C), e.g. by foliar application. Treatment with component (A) and optionally (C) can take place during the whole lifetime of the plant, i.e. until harvesting of the plant or until the natural death of the plant. In terms of the BBCH extended scale; German Federal Biological Research Centre for Agriculture and Forestry; see www.bba.de/veroeff/bbch/bbcheng.pdf, treatment with component (A) and optionally (C) is preferably carried out in the period starting from emergence, i.e. when the plants are in the growth stage BBCH 09, and ending with the death of the plant, i.e. BBCH stage 99, or, if the plant or its fruit/crop are harvested, ending with the ripening of the plant or its fruit/crop, i.e. BBCH stage 89.

More preferably, the treatment with component (A) and optionally (C) is carried out during the vegetative period of the plant, i.e. starting with emergence (BBCH stage 09) and ending before inflorescence starts (BBCH stage 49).

In an alternatively more preferred embodiment, the treatment with component (A) and optionally (C) is carried out after the vegetative period of the plant, i.e. during inflorescence or flowering and/or even later, for example during the fruit development.

In an alternatively more preferred embodiment, one treatment with component (A) and optionally (C) is carried out during the vegetative period of the plant, i.e. starting with emergence (BBCH stage 09) and ending before inflorescence starts (BBCH stage 49), and at least one further treatment is carried out during inflorescence or flowering and/or even later, for example during the fruit development.

The treatment of the plant with component (A) and optionally (C) can be carried out once or several times, e.g. 1, 2, 3 or 4 times, preferably 1, 2 or 3 times, more preferably 1 or 2 times and in particular once.

If component (C) is applied, it is preferably applied simultaneously with component (A), either as a physical mixture or formulated separately, the first variant being preferred.

Propagules are all types of plant propagation material. The term embraces seeds, grains, fruit, tubers, rhizomes, spores, cuttings, offshoots, meristem tissues, single and multiple plant cells and any other plant tissue from which a complete plant can be obtained. One particular propagule is seed.

In the context of the present invention, parts of the plant refer to overground parts, such as leaves, stem, blossoms, flowers, fruit and the like. Treatment of the plant refers to treating the whole plant, specifically the whole overground part of the plant, but also only overground parts of the plant, such as the leaves.

Locus means soil, area, material or environment where the plant is growing or intended to grow.

As a matter of course, components (A) and (B) and the optional component (C) are used in an effective and non-phytotoxic amount. This means that they are used in a quantity which allows to obtain the desired effect but which does not give rise to any phytotoxic symptom on the treated plant or on the plant raised from the treated propagule or treated soil.

The plants to be treated are generally plants of economic importance and/or men-grown plants. Thus, they are preferably selected from agricultural, silvicultural and ornamental plants.

"Plant health" is intended to mean a condition of the plant which is determined by several aspects alone or in combination with each other. One indicator (indicator 1) for the condition of the plant is the crop yield. "Crop" and "fruit" are to be understood as any plant product which is further utilized after harvesting, e.g. fruits in the proper sense, vegetables, nuts, grains, seeds, wood (e.g. in the case of silviculture plants), flowers (e.g. in the case of gardening plants, ornamentals) etc., that is anything of economic value that is produced by the plant. Another indicator (indicator 2) for the condition of the plant is the plant vigour. The plant vigour becomes manifest in several aspects, too, some of which are visual appearance, e.g. leaf color, fruit color and aspect, amount of dead basal leaves and/or extent of leaf blades, plant weight, plant height, extent of plant verse (lodging), number, strongness and productivity of tillers, panicles' length, extent of root system, strongness of roots, extent of nodulation, in particular of rhizobial nodulation, point of time of germination, emergence, flowering, grain maturity and/or senescence, protein content, sugar content and the like. Another indicator (indicator 3) for the condition of the plant is the plant's tolerance or resistance to biotic and abiotic stress factors.

Biotic and abiotic stress, especially over longer terms, can have harmful effects on plants. Biotic stress is caused by living organisms, such as pests (e.g. insects, arachnides, nematodes etc.), competing plants (for example weeds), phytopathogenic fungi and other microorganisms such as bacteria and viruses. Abiotoc stress is caused for example by extremes in temperature such as heat or cold or strong variations in temperature or temperatures unusual for the specific season, drought, extreme wetness, high salinity, radiation (e.g. increased UV radiation due to the decreasing ozone protective layer), increased ozone levels and organic pollution (e.g. by phythotoxic amounts of pesticides) or inorganic pollution (e.g. by heavy metal contaminants). As a result, the quantity and the quality of the stressed plants, their crops and fruits decrease. As far as quality is concerned, reproductive development is usually severely affected with consequences on the crops which are important for fruits or seeds. Synthesis, accumulation and storage of proteins are mostly affected by temperature; growth is slowed by almost all stresses; polysaccharide synthesis, both structural and storage, is reduced or modified: these effects bring to a decrease in biomass and to changes in the nutritional value of the product.

Of course, the three above indicators for the health condition of a plant may be interdependent and may result from each other. For example, an increased resistance to biotic and/or abiotic stress may lead to a better plant vigor, e.g. to better and bigger crops, and thus to an increased yield. Inversely, a more developed root system may result in an increased resistance to biotic and/or abiotic stress. However, these inter-dependecies and interactions are neither all known nor fully understood and therefore the different indicators will be described separately.

In one preferred embodiment, the present invention provides the use of the composition of the invention for increasing the yield of a plant, preferably of an agricultural, silvicultural and/or ornamental plant.

The present invention further provides a method for increasing the yield of a plant, preferably of an agricultural, silvicultural and/or ornamental plant, which comprises treating the plant, the locus where the plant is growing or is expected to grow, and/or the propagules from which the plant grows with a composition of the invention. According to this inventive method the plant, the locus where the plant is growing or is expected to grow, and/or the propagules from which the plant grows are treated simultaneously (together or separately) or—preferably—subsequently with the components (A) and (B) and optionally (C). Of course, the subsequent application is carried out with a time interval which allows a combined action of the two or three components. Preferably, the time interval for a subsequent application of components (A) and (B) and optionally (C) ranges from a few seconds up to several months. For more details to preferred embodiments of the subsequent application reference is made to what has been said above.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the invention. According to the present invention, it is preferred that the yield be increased by at least 0.5%, more preferred at least 1%, even more preferred at least 2%, still more preferred at least 4%.

In another preferred embodiment, the present invention provides the use of the composition of the invention for increasing the yield and/or improving the vigor of a plant, e.g. of an agricultural, silvicultural and/or ornamental plant.

The present invention further provides a method for increasing the yield and/or improving the vigor of a plant, which comprises treating the plant, the locus where the plant is growing or is expected to grow, and/or the propagules from which the plant grows with the composition of the invention. According to this inventive method the plant, the locus where the plant is growing or is expected to grow, and/or the propagules from which the plant grows are treated simultaneously (together or separately) or—preferably subsequently with the components (A) and (B) and optionally (C). Of course, the subsequent application is carried out with a time interval which allows a combined action of the two or three components. Preferably, the time interval for a subsequent application of components (A) and (B) and optionally (C) ranges from a few seconds up to several months. For more details to preferred embodiments of the subsequent application reference is made to what has been said above.

According to the present invention, "improved plant vigor" means that certain crop characteristics are increased or improved by a measurable or noticeable amount over the same factor of the plant produced under the same conditions, but without the application of the composition of the present invention.

Improved plant vigor can be characterized, among others, by following improved properties of the plant:
(a) improved vitality of the plant,
(b) improved quality of the plant and/or of the plant products, e.g.
  (b.1) enhanced protein content,
(c) improved visual appearance,
(d) delay of senescence,
(e) enhanced root growth and/or more developed root system (e.g. determined by the dry mass of the root),
(f) enhanced nodulation, in particular rhizobial nodulation,
(g) longer panicles,
(h) bigger leaf blade,
(i) less dead basal leaves,
(j) increased chlorophyll content
(k) prolonged photosynthetically active period
(l) increased or improved plant stand density,
(m) less plant verse (lodging),
(n) increased plant weight,
(o) increased plant height,
(p) tillering increase,
(q) stronger and/or more productive tillers,
(r) less non-productive tillers,
(s) enhanced photosynthetic activity and/or enhanced pigment content and thus
  (q.1) greener leaf color,
(t) earlier and/or improved germination,
(u) improved and/or more uniform and/or earlier emergence,
(v) increased shoot growth,
(w) earlier flowering,
(x) earlier fruiting,
(y) earlier grain maturity,
(z) less fertilizers needed,
(aa) less seeds needed.

The improvement of the plant vigor according to the present invention particularly means that the improvement of any one or several or all of the above mentioned plant characteristics are improved independently of the pesticidal action of the composition or active ingredients. It further means that if not all of the above characteristics are improved, those which are not improved are not worsened as compared to plants which were not treated according to the invention or are at least not worsened to such an extent that the negative effect exceeds the positive effect of the improved characteristic (i.e. there is always an overall positive effect which preferably results in an improved crop yield).

In a more preferred embodiment of the invention, the composition of the invention is used for enhancing root growth and/or inducing the formation of a more developed root system of a plant. This effect can for example be measured by determining the dry mass of the root. The enhanced root growth and the formation of a more developed root system is to be understood as a mean value over the whole lifetime of the plant, i.e. from emergence till death/harvesting.

In another more preferred embodiment of the invention, the composition of the invention is used for enhancing nodulation, in particular rhizobial nodulation. The enhanced nodulation is to be understood as a mean value over the whole lifetime of the plant, i.e. from emergence till death/harvesting of the plant.

In another more preferred embodiment of the invention, the composition of the invention is used for enhancing the chlorophyll content of the plant. The enhanced chlorophyll content is to be understood as a mean value over the whole lifetime of the plant, i.e. from emergence till death/harvesting of the plant.

In another more preferred embodiment of the invention, the composition of the invention is used for prolongating the photosynthetically active period of the plant. The photosynthetically active period of the plant generally lasts from the emergence of the first true leaf till the death of the plant or the beginning of loss of the green color of the foliage or, if there is no color change of the leaves, the beginning of leaf-fall. The prolongation of the photosynthetically active period of the plant can be due to several factors, such as an earlier emergence (not exceeded by a possible earlier senescence) and a delayed senescence (not exceeded by a possible later emergence). A prolonged photosynthetically active period means a prolonged time for carbon assimilation, generally resulting in a higher crop yield.

In another more preferred embodiment of the invention, the composition of the invention is used for obtaining an improved and/or more uniform and/or earlier emergence. Improved emergence means that the plant propagules give rise to more plants emerging therefrom, as compared to the same number of plant propagules of the same plant variety which or the locus of which have not been treated according to the invention. More uniform emergence refers to the time period within which the plants or the majority of the plants (preferably 90% of the plants which emerge) emerge. Earlier emergence means that the mean time which elapses from placing the plant propagule into the growing medium (e.g. by sowing) until the young plant (cotyledon/coleoptile/shoot/leaf) breaks through the surface of the growing medium (emergence) is shorter than for plants which have not been treated according to the invention.

In another more preferred embodiment of the invention, the composition of the invention is used for delaying senescence (which is not exceeded by a delayed emergence). A delayed senescence means a longer lifetime of the plant, which, due to the prolonged time for carbon and/or nitrogen assimilation, generally results in a higher crop yield.

In an even more preferred embodiment of the invention, the composition of the invention is used for obtaining at least one and preferably at least two of the following characteristics: enhanced chlorophyll content; prolongated photosynthetically active period; improved and/or more uniform and/or earlier emergence; delayed senescence of the plant.

The above characteristics, each taken alone or in combination with each other, result in an extended crop life cycle. An extended crop life cycle generally means a prolonged carbon and/or nitrogen assimilation of the plant which finally results in an enhanced crop yield.

In yet another preferred embodiment, the present invention provides the use of the composition of the invention for enhancing the plant's tolerance or resistance to biotic and/or abiotic stress factors.

The present invention further provides a method for enhancing a plant's tolerance or resistance to biotic and/or abiotic stress factors, which comprises treating the plant, the locus where the plant is growing or is expected to grow, and/or the propagules from which the plant grows with the composition of the invention. According to this inventive method, the plant, the locus where the plant is growing or is expected to grow, and/or the propagules from which the plant grows are treated simultaneously (together or separately) or—preferably—subsequently with the components (A) and (B) and optionally (C). Of course, the subsequent application is carried out with a time interval which allows a combined action of the two or three components. Preferably, the time interval for a subsequent application of components (A) and (B) and optionally (C) ranges from a few seconds up to several months, preferably, from a few seconds up to 12 month. For more details to preferred embodiments of the subsequent application reference is made to what has been said above.

Biotic and abiotic stress factors have been defined above.

According to the present invention, "enhanced plant's tolerance or resistance to biotic and/or abiotic stress factors" means (1.) that certain negative factors caused by biotic and/or abiotic stress are diminished in a measurable or noticeable amount as compared to plants exposed to the same conditions, but without being treated with the composition of the invention and (2.) that the negative effects are not diminished by a direct action of the composition on the stress factors, e.g. by its fungicidal or insecticidal action which directly destroys the microorganisms or pests, but rather by a stimulation of the plants' own defensive reactions against said stress factors.

Negative factors caused by biotic stress such as pathogens and pests are widely known and range from dotted leaves to total destroyment of the plant.

Negative factors caused by abiotic stress are also well-known and can often be observed as reduced plant vigor (see above), e.g. dotted leaves, "burned leaves", reduced growth, less flowers, less biomass, less crop yields, reduced nutritional value of the crops, later crop maturity, to give just a few examples.

In one preferred embodiment, the tolerance of and/or resistance against biotic stress factors is enhanced. Thus, according to a preferred embodiment of the present invention, the inventive compositions are used for stimulating the natural defensive reactions of a plant against a pathogen and/or a pest. Thereby, the plant can be protected against unwanted microorganisms such as phytopathogenic fungi, bacteria or viruses and/or against pests such as insects, arachnids and nematodes, and it has been found that the inventive compositions result in plant strengthening effects. Therefore, they are useful for mobilizing the plant's defense mechanisms against the attack of unwanted microorganisms and/or pests. Consequently, the plant becomes tolerant or even resistant towards these microorganisms and/or pests. Unwanted microorganisms in this context are phytopathogenic fungi and/or bacteria and/or viruses. Unwanted pests are insects and/or arachnids and/or nematodes. Preferably the inventive compositions are used for stimulating the natural defensive reactions of a plant against microorganisms and more preferably against phytopathogenic fungi, bacteria and/or viruses, wherein, according to the present invention, the treated plant may develop increased defense mechanism against one of these pathogens or against two, three or all of these pathogens.

In another preferred embodiment, the tolerance of and/or resistance against abiotic stress factors is enhanced. Thus, according to a further embodiment of the present invention, the inventive compositions are used for stimulating a plant's own defensive reactions against abiotic stress such as extremes in temperature, e.g. heat or cold or strong variations in temperature or temperatures unusual for the specific season, drought, extreme wetness, high salinity, radiation (e.g. increased UV radiation due to the decreasing ozone protective layer), increased ozone levels, organic pollution (e.g. by phythotoxic amounts of pesticides) and/or inorganic pollution (e.g. by heavy metal contaminants).

In a more preferred embodiment, the inventive compositions are used for stimulating a plant's own defensive reactions against abiotic stress, where the abiotic stress factors are preferably selected from extremes in temperature, drought and extreme wetness.

In another more preferred embodiment, the inventive compositions are used for reducing or inhibiting the injury caused to plants by phytotoxic amounts of pesticides such as fungicides, herbicides and/or insecticides.

Enhancing the plant's tolerance or resistance to biotic and/or abiotic stress factors generally also results in an enhanced crop yield.

In one embodiment of the invention, the plant the health of which is to be improved by the treatment with the composition of the invention is an agricultural plant. Agricultural plants are plants of which a part or all is harvested or cultivated on a commercial scale or which serve as an important source of feed, food, fibers (e.g. cotton, linen), combustibles (e.g. wood, bioethanol, biodiesel, biomass) or other chemical compounds. Agricultural plants also horticultural plants, i.e. plants grown in gardens (and not on fields), such as certain fruits and vegetables. Examples for agricultural plants are soybean, corn (maize), wheat, triticale, barley, oats, rye, rape, such as canola/oilseed rape, millet (sorghum), rice, sunflower, cotton, sugar beets, pome fruit, stone fruit, citrus, bananas, strawberries, blueberries, almonds, grapes, mango, papaya, peanuts, potatoes, tomatoes, peppers, cucurbits, cucumbers, melons, watermelons, garlic, onions, carrots, cabbage, beans, peas, lentils, alfalfa (lucerne), trefoil, clovers, flax, elephant grass (Miscanthus), grass, lettuce, sugar cane, tea, tobacco and coffee.

Preferably, the agricultural plants are selected from triticale, barley, oats, rye, rape, such as canola/oilseed rape, millet (sorghum), rice, sunflower and sugar cane and more preferably from soybean, corn (maize), wheat and rape, such as canola/oilseed rape. In particular, the agricultural plant is soybean (transgenic or non-transgenic).

Alternatively, the agricultural plants are selected from potatoes, tomatoes, peppers, cucurbits, cucumbers, melons, watermelons, garlic, onions, carrots, cabbage, beans, peas and lettuce and more preferably from tomatoes, onions, peas and lettuce.

In another embodiment of the invention, the plant the health of which is to be improved by the treatment with the composition of the invention is a silvicultural plant. Silviculturel plants in the terms of the present invention are trees, more specifically trees used in reforestation or industrial plantations. Industrial plantations generally serve for the commercial production of forest products, such as wood, pulp, paper, rubber, Christmas trees, or young trees for gardening purposes. Examples for silviculturel plants are conifers, like pines, in particular *Pinus* spec., fir and spruce, eucalyptus, tropical trees like teak, rubber tree, oil palm, willow (*Salix*), in particular *Salix* spec., poplar (cottonwood), in particular *Popolus* spec., beech, in particular *Fagus* spec., birch and oak.

In another embodiment of the invention, the plant the health of which is to be improved by the treatment with the composition of the invention is an ornamental plant. Ornamental plants are plants which are commonly used in gardening, e.g. in parks, gardens and on balconies. Examples are turf, geranium, pelargonia, petunia, begonia, and fuchsia, to name just a few among the vast number of ornamentals.

The plants can be non-transgenic plants or can be plants that have at least one transgenic event. In one embodiment, the plant is a transgenic plant having a transgenic event that confers resistance to a pesticide. Examples for transgenic plants having a pesticide resistance are transgenic crops which are resistant to herbicides from the group consisting of the sulfonylureas (see for example EP-A-0257993, U.S. Pat. No. 5,013,659), imidazolinones (see for example U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or plants resistant towards herbicides selected from the group of cyclohexadienone/aryloxyphenoxypropionic acid herbicides (see for example U.S. Pat. No. 5,162,602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or transgenic crop plants, for example cotton, with the capability of producing *Bacillus thuringiensis* toxins (Bt toxins) which make the plants resistant to certain pests (see for example EP-A-0142924, EP-A-0193259).

It is to be understood, however, that when the plant is a transgenic plant, the transgenic events that are present in the plant are by no means limited to those that provide pesticide resistance, but can include any transgenic event. In fact, the use of "stacked" transgenic events in a plant is also contemplated.

The treatment of a plant or its growth locus or its propagation material, such as a seed, with the composition of the invention can be accomplished in several ways. The components (A) and/or (B) and optionally (C) may be applied directly to the propagules, especially the seed, and/or to the soil in which the seed is to be planted, for example, at the time of planting along with the seed (for example in-furrow application). Alternatively, they may be applied to the soil after planting and germination or to the foliage of the plant after emergence and/or during the whole life cycle of the plant.

Preferably, one of the components (A) or (B) is applied to the propagation material and/or to the growing medium in which the propagule is to be planted, and preferably to the propagation material, and the other component is applied to the plant, i.e. after its emergence. If component (C) is to be applied, too, application takes preferably place together with one of components (A) or (B), preferably (A).

In a more preferred embodiment, the propagules from which the plant (i.e. the plant the health of which is to be improved) is to grow are treated with component (B). After emergence, i.e. after the young plant has broken through the surface of the growing medium, the plant is then treated once or several times with component (A) and optionally with component (C), e.g. by foliar application. Treatment with component (A) and optionally (C) can take place during the whole lifetime of the plant, i.e. until harvesting of the plant or until the natural death of the plant. In terms of the BBCH extended scale; German Federal Biological Research Centre for Agriculture and Forestry; see www.bba.de/veroeff/bbch/bbcheng.pdf, treatment with component (A) and optionally (C) is preferably carried out in the period starting from emergence, i.e. when the plants are in the growth stage BBCH 09, and ending with the death of the plant, i.e. BBCH stage 99, or, if the plant or its fruit/crop are harvested, ending with the ripening of the plant or its fruit/crop, i.e. BBCH stage 89. More preferably, the treatment with component (A) and optionally (C) is carried out during the vegetative period of the plant, i.e. starting with emergence (BBCH stage 09) and ending before inflorescence starts (BBCH stage 49). In an alternatively more preferred embodiment, one treatment with component (A) and optionally (C) is carried out during the vegetative period of the plant, i.e. during the period which starts with emergence (BBCH stage 09) and ends before inflorescence starts (BBCH stage 49), and at least one further treatment is carried out during inflorescence or flowering and/or even later, for example during the fruit development.

The treatment of the plant with component (A) and optionally (C) can be carried out once or several times, e.g. 1, 2, 3 or 4 times, preferably 1, 2 or 3 times and more preferably 1 or 2 times and specifically once. If the treatment with component (A) and optionally (C) is to be carried out only once, this is preferably done during the vegetative period of the plant, i.e. during the period which starts with emergence (BBCH stage 09) and ends before inflorescence starts (BBCH stage 49). Alternatively preferably, this is preferably done after the vegetative period of the plant, i.e. during the period which starts with inflorescence (BBCH stage 51) and ends preferably before the ripening of the fruit begins (BBCH stage 79).

If component (C) is applied, it is preferably applied simultaneously with component (A), either as a physical mixture or formulated separately, the first variant being preferred.

By "germination" is meant observable root growth development from the embryo and by "emergence" observable growth above the rooting medium surface (mostly above soil surface). To be more precise, "emergence" means that the coleoptile/cotyledon/shoot/leaf breaks through the soil surface.

The components (A) and (B) and the optional component (C) of the composition of the invention can be applied as such, in the form of their formulations or the application form prepared therefrom, for example in the form of directly sprayable solutions, powders, suspensions or dispersions, including highly concentrated aqueous, oily or other suspensions or dispersions, emulsions, oil dispersions, pastes, dusts, compositions for broadcasting or granules. Application is usually carried out by spraying, atomizing, dusting, broadcasting or watering. The application forms and methods depend on the intended uses; in each case, they should ensure the finest possible distribution of the active compounds.

Depending on the embodiment in which the ready-to-use preparations of the components (A) and (B) and the optional component (C) are present, they comprise one or more liquid or solid carriers, if appropriate surfactants and if appropriate further auxiliaries customary for formulating crop protection agents. The recipes for such formulations are familiar to the person skilled in the art.

Aqueous application forms can be prepared, for example, from emulsion concentrates, suspensions, pastes, wettable powders or water-dispersible granules by addition of water. To prepare emulsions, pastes or oil dispersions, the active components (A) and (B) and the optional component (C), as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, such concentrates being suitable for dilution with water.

The concentrations of components (A) and (B) and the optional component (C) in the ready-to-use preparations can be varied within relatively wide ranges. In general, they are between 0.0001 and 10%, preferably between 0.01 and 1% (% by weight total content of active compounds of groups (A) and (B) and optionally (C), based on the total weight of the ready-to-use preparation).

The components (A) and (B) and the optional component (C) of the composition of the invention may also be used successfully in the ultra-low-volume process (ULV), it being possible to employ formulations comprising more than 95% by weight of total active compound, or even to apply the active compounds without additives.

Oils of various types, wetting agents, adjuvants, herbicides, fungicides and insecticides different from active compounds I of component A, from the azole fungicides of the optional component (C) and the insecticides of component (B), nematicides, other pesticides, such as bactericides, fertilizers and/or growth regulators may be added to the active compounds, even, if appropriate, not until immediately prior to use (tank mix). These agents can be mixed in a weight ratio of from 1:100 bis 100:1, preferably from 1:10 to 10:1 with the active compounds (A) and (B) and optionally (C) employed according to the invention.

Adjuvants are for example: modified organic polysiloxanes, e.g. Break Thru S 240®; alkohol alkoxylates, e.g. Atplus 245®, Atplus MBA 1303®, Plurafac LF 300® and Lutensol ON 30®; EO-PO block copolymers, e.g. Pluronic RPE 2035® and Genapol B®; alkohol ethoxylates, e.g. Lutensol XP 80®; and sodium dioctylsulfosuccinate, e.g. Leophen RA®.

Suitable insecticides are for example:
organophosphates such as acephate, azinphos-methyl, chlorpyrifos, chlorfenvinphos, diazinon, dichlorvos, dicrotophos, dimethoate, disulfoton, ethion, fenitrothion, ffenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, triazophos, trichlorfon;
carbamates such as alanycarb, benfuracarb, carbaryl, carbosulfan, fenoxycarb, furathiocarb, indoxacarb, methiocarb, methomyl, oxamyl, pirimicarb, propoxur, thiodicarb, triazamate, carbofuran;
pyrethroids such as bifenthrin, cyfluthrin, cypermethrin, deltamethrin, esfenvalerate, ethofenprox, fenpropathrin, fenvalerate, cyhalothrin, lambda-cyhalothrin, permethrin, silafluofen, tau-fluvalinate, tefluthrin, tralomethrin, zeta-cypermethrin;
arthropod growth regulators such as a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide; c) juvenoids: pyriproxyfen, methoprene, fenoxycarb; d) lipid biosynthesis inhibitors: spirodiclofen;

various such as abamectin, acequinocyl, acetamiprid, amitraz, azadirachtin, bifenazate, cartap, chlorfenapyr, chlordimeform, cyromazine, diafenthiuron, dinetofuran, diofenolan, emamectin, endosulfan, fenazaquin, formetanate, formetanate hydrochloride, hydramethylnon, imidacloprid, indoxacarb, pyridaben, pymetrozine, spinosad, sulfur, tebufenpyrad, thiamethoxam, and thiocyclam.

Suitable fungicides are for example:

acylalanines such as benalaxyl, metalaxyl, ofurace, oxadixyl;

amine derivatives such as aldimorph, dodine, dodemorph, fenpropimorph, fenpropidin, guazatine, iminoctadine, spiroxamin, tridemorph; vanilinopyrimidines such as pyrimethanil, mepanipyrim or cyrodinyl;

antibiotics such as cycloheximid, griseofulvin, kasugamycin, natamycin, polyoxin or streptomycin;

dicarboximides such as iprodion, myclozolin, procymidon, vinclozolin;

dithiocarbamates such as ferbam, nabam, maneb, mancozeb, metam, metiram, propineb, polycarbamate, thiram, ziram, zineb;

heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

copper fungicides such as Bordeaux mixture, copper acetate, copper oxychloride, basic copper sulfate;

nitrophenyl derivatives such as binapacryl, dinocap, dinobuton, nitrophthalisopropyl;

phenylpyrroles such as fenpiclonil or fludioxonil;

sulfur other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid;

strobilurins such as azoxystrobin, dimoxystrobin, fluoxastrobin, kresoxim-methyl, metominostrobin, orysastrobin, picoxystrobin or trifloxystrobin;

sulfenic acid derivatives such as captafol, captan, dichlofluanid, folpet, tolylfluanid;

cinnemamides and analogs such as dimethomorph, flumetover or flumorph.

Preferred fungicides are those selected from the group consisting of:

acylalanines such as benalaxyl, metalaxyl, ofurace, oxadixyl;

dicarboximides such as iprodion, myclozolin, procymidon, vinclozolin;

dithiocarbamates such as ferbam, nabam, maneb, mancozeb, metam, metiram, propineb, polycarbamate, thiram, ziram, zineb;

heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine;

other fungicides such as acibenzolar-S-methyl, benthiavalicarb, carpropamid, chlorothalonil, cyflufenamid, cymoxanil, dazomet, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid;

strobilurins such as azoxystrobin, dimoxystrobin, fluoxastrobin, kresoxim-methyl, metominostrobin, orysastrobin, picoxystrobin or trifloxystrobin; sulfenic acid derivatives such as captafol, captan, dichlofluanid, folpet, tolylfluanid;

cinnemamides and analogs such as dimethomorph, flumetover or flumorph.

More preferred fungicides are those selected from:

metalaxyl;

iprodione;

thiram;

benomyl, boscalid, carbendazin, carboxin, thiabendazole, thiophanate-methyl;

metrafenone, penycuron;

dimoxystrobin;

captan; and dimethomorph.

The formulations are prepared in a known manner, for example by extending the active compounds with solvents and/or carriers, if desired with the use of surfactants, i.e. emulsifiers and dispersants. Solvents/carriers suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, methyl hydroxybutyl ketone, diacetone alcohol, mesityl oxide, isophorone), lactones (for example gamma-butyrolactone), pyrrolidones (pyrrolidone, N-methylpyrrolidone, Methylpyrrolidone, n-octylpyrrolidone), acetates (glycol diacetate), glycols, dimethyl fatty acid amides, fatty acids and fatty acid esters. In principle, solvent mixtures may also be used.

Carriers such as ground natural minerals (for example kaolins, clays, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates), and dispersants such as lignosulfite waste liquors and methylcellulose.

Suitable surfactants are alkali metal salts, alkaline earth metal salts and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenyl polyglycol ether, tributylphenyl polyglycol ether, tristerylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable and animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, mesityl oxide, isophorone, strongly polar solvents, for example dimethyl sulfoxide, 2-yrrolidone, N-methylpyrrolidone, butyrolactone, or water.

Powders, compositions for broadcasting and dusts can be prepared by mixing or jointly grinding the active substances with a solid carrier.

Granules, for example coated granules, impregnated granules and homogeneous granules, can be prepared by binding the active compounds onto solid carriers. Solid carriers are, for example, mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and plant products such as cereal meal, tree bark meal, wood meal and nutshell meal, cellulose powder and other solid carriers.

Formulations for seed treatment can further comprise binders and/or gelling agents and optionally colorants.

In general, the formulations comprise between 0.01 and 95% by weight, preferably between 0.1 and 90% by weight, in particular 5 to 50% by weight, of the active compounds (total weight). In this context, the active compounds are employed in a purity of from 90% to 100%, preferably 95% to 100% (according to NMR spectrum).

After two- to ten-fold dilution, formulations for seed treatment comprise 0.01 to 60% by weight, preferably 0.1 to 40% by weight of the active compounds (total weight) in the ready-to-use preparations.

Examples of formulations are:
1. Products for Dilution in Water
  I) Water-Soluble Concentrates (SL, LS)
  10 parts by weight of active compounds are dissolved in 90 parts by weight of water or a water-soluble solvent. Alternatively, wetting agents or other adjuvants are added. Upon dilution in water, the active compound dissolves. The ready formulation contains 10% by weight of active ingredients.
  II) Dispersible Concentrates (DC)
  20 parts by weight of active compounds are dissolved in 70 parts by weight of cyclohexanone with addition of 10 parts by weight of a dispersant, for example polyvinylpyrrolidone. The active ingredients are contained in 20% by weight. Upon dilution in water, a dispersion results.
  III) Emulsifiable Concentrates (EC)
  15 parts by weight of active compounds are dissolved in 75 parts by weight of xylene with addition of calcium dodecylbenzenesulfonate and castor oil ethoxylate (in each case 5 parts by weight). The active ingredients are contained in 15% by weight. Upon dilution in water, an emulsion results.
  IV) Emulsions (EW, EO, ES)
  25 parts by weight of active compounds are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. The active ingredients are contained in 25% by weight. Upon dilution in water, an emulsion results.
  V) Suspensions (SC, OD, FS)
  20 parts by weight of active compounds are comminuted in a stirred ball mill with addition of 10 parts by weight of dispersants, wetting agents and 70 parts by weight of water or an organic solvent to give a fine suspension of active compound. The active ingredients are contained in 20% by weight. Upon dilution in water, a stable suspension of the active compound results.
  VI) Water-Dispersible and Water-Soluble Granules (WG, SG)
  50 parts by weight of active compounds are ground finely with addition of 50 parts by weight of dispersants and wetting agents and made into water-dispersible or water-soluble granules by means of technical apparatuses (for example extrusion, spray tower, fluidized bed). The active ingredients are contained in 50% by weight. Upon dilution in water, a stable dispersion or solution of the active compound results.
  VII) Water-Dispersible and Water-Soluble Powders (WP, SP, SS, WS)
  75 parts by weight of active compounds are ground in a rotor-stator mill with addition of 25 parts by weight of dispersants, wetting agents and silica gel. The active ingredients are contained in 75% by weight. Upon dilution in water, a stable dispersion or solution of the active compound results.
  VIII) Gel Formulations (GF)
  20 parts by weight of active compounds, 10 parts by weight of dispersants, 1 part by weight of gelling agent and 70 parts by weight of water or an organic solvent are ground in a ball mill to give a finely divided suspension. Upon dilution in water, a stable suspension of the active compounds results.
2. Products for Direct Application
  IX) Dusts (DP, DS)
  5 parts by weight of active compounds are ground finely and mixed intimately with 95 parts by weight of finely particulate kaolin. This gives a dust with 5% by weight of active ingredients.
  X) Granules (GR, FG, GG, MG)
  0.5 part by weight of active compounds is ground finely and combined with 95.5 parts by weight of carriers. Current methods are extrusion, spray drying or the fluidized bed. This gives granules for direct application with 0.5% by weight of active ingredients.
  XI) ULV Solutions (UL)
  10 parts by weight of active compounds are dissolved in 90 parts by weight of an organic solvent, for example xylene. This gives a product for direct application with 10% by weight of active ingredients.

Formulations suitable for treating seed are, for example:
I soluble concentrates (SL, in particular LS)
III emulsifiable concentrates (EC)
IV emulsions (EW, EO, in particular ES)
V suspensions (SC, OD, in particular FS)
VI water-dispersible and water-soluble granules (WG, in particular SG)
VII water-dispersible and water-soluble powders (WP, in particular SS and WS)
VIII gel formulations (GF)
IX dusts and dust-like powders (DP, in particular DS)

Preferred formulations to be used for seed treatment are FS formulations. Generally, theses formulations comprise 1 to 800 g/l of active compounds, 1 to 200 g/l of wetting agents, 0 to 200 g/l of antifreeze agents, 0 to 400 g/l of binders, 0 to 200 g/l of colorants (pigments and/or dyes) and solvents, preferably water.

Preferred FS formulations of the active compounds for the treatment of seed usually comprise from 0.5 to 80% of active compounds, from 0.05 to 5% of wetting agent, from 0.5 to 15% of dispersant, from 0.1 to 5% of thickener, from 5 to 20% of antifreeze agent, from 0.1 to 2% of antifoam, from 1 to 20% of pigment and/or dye, from 0 to 15% of tackifier or adhesive, from 0 to 75% of filler/vehicle, and from 0.01 to 1% of preservative.

Suitable pigments or dyes for formulations of the active compounds for the treatment of seed are Pigment blue 15:4, Pigment blue 15:3, Pigment blue 15:2, Pigment blue 15:1, Pigment blue 80, Pigment yellow 1, Pigment yellow 13, Pigment red 112, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108.

Suitable wetting agents and dispersants are in particular the surfactants mentioned above. Preferred wetting agents are alkylnaphthalenesulfonates, such as diisopropyl- or diisobutylnaphthalenesulfonates. Preferred dispersants are nonionic or anionic dispersants or mixtures of nonionic or anionic dispersants. Suitable nonionic dispersants are in particular ethylene oxide/propylene oxide block copolymers, alkylphenol polyglycol ethers and also tristryrylphenol polyglycol ether, for example polyoxyethylene octylphenol ether, ethoxylated isooctylphenol, octylphenol, nonylphenol, alkylphenol polyglycol ethers, tributylphenyl polyglycol ether, tristerylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters and methylcellulose. Suitable anionic dispersants are in particular alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore arylsulfonate/formaldehyde condensates, for example condensates of sulfonated naphthalene and naphthalene derivatives with formaldehyde, condensates of naphthalene or of naphthalenesulfonic acid with phenol and formaldehyde, lignosulfonates, lignosulfite waste liquors, phosphated or sulfated derivatives of methylcellulose and polyacrylic acid salts.

Suitable for use as antifreeze agents are, in principle, all substances which lower the melting point of water. Suitable antifreeze agents include alkanols, such as methanol, ethanol, isopropanol, the butanols, glycol, glycerol, diethylene glycol and the like.

Suitable thickeners are all substances which can be used for such purposes in agrochemical compositions, for example cellulose derivatives, polyacrylic acid derivatives, xanthane, modified clays and finely divided silica.

Suitable for use as antifoams are all defoamers customary for formulating agrochemically active compounds. Particularly suitable are silicone antifoams and magnesium stearate.

Suitable for use as preservatives are all preservatives which can be employed for such purposes in agrochemical compositions. Dichlorophene, isothiazolenes, such as 1,2-benzisothiazol-3(2H)-one, 2-methyl-2H-isothiazol-3-one hydrochloride, 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one calcium chloride complex, 2-octyl-2H-isothiazol-3-one, and benzyl alcohol hemiformal may be mentioned by way of example.

Adhesives/tackifiers are added to improve the adhesion of the effective components on the seed after treating. Suitable adhesives are EO/PO-based block copolymer surfactants, but also polyvinyl alcohols, polyvinyl pyrrolidones, polyacrylates, polymethacrylates, polybutenes, polyisobutenes, polystyrene, polyethyleneamines, polyethyleneamides, polyethyleneimines (Lupasol®, Polymin®), polyethers and copolymers derived from these polymers.

One example for a suitable gelling agent is carrageen.

Suitable compositions for soil treatment include granules which may be applied in-furrow, as broadcast granules or as impregnated fertilizer granules, and also spray applications which are applied to the soil as a preemergent or postemergent spray.

Suitable compositions for treating the plants, in particular the overground parts thereof, especially the leaves (=foliar application) include spray applications, dusts and microgranules, spray applications being preferred.

Formulations suitable for producing spray solutions for the direct application are:

I soluble concentrates (SL, LS)

II dispersible concentrates (DC)

III emulsifiable concentrates (EC)

IV emulsions (EW, EO)

V suspensions (SC)

VI water-dispersible and water-soluble granules (WG)

VII water-dispersible and water-soluble powders (WP, SP)

The required application rate of pure composition of the invention, i.e. components (A) and (B) and the optional component (C) without formulation auxiliaries depends on the composition of the plant stand, on the development stage of the plants, on the climatic conditions at the application site and on the application method. In general, the total amount of components (A) and (B) and the optional component (C) applied is from 0.001 to 3 kg/ha, preferably from 0.005 to 2 kg/ha and in particular from 0.01 to 1 kg/ha of active substances (a.s.).

In the treatment of seed, the total amount of components (A) and (B) and the optional component (C) used is from 0.1 to 1000 g/100 kg of seed, preferably from 0.1 to 200 g/100 kg, in particular from 1 to 100 g/100 kg.

The methods of the invention are generally carried out by bringing the plant to be treated, parts of plant, the locus where the plant is growing or is intended to grow and/or its propagules in contact with the composition of the invention or with a formulation comprising it. To this end, the mixture or the individual active components (A) and (B) are applied to the plant, parts of plant, the locus where the plant is growing or is intended to grow and/or its propagules. As regards preferred embodiments of the method of the invention, reference is made to what has been said above about the application of the single components (A), (B) and (C).

For treating the propagules, in particular the seed, it is possible in principle to use any customary methods for treating or dressing seed, such as, but not limited to, seed dressing, seed coating, seed dusting, seed soaking, seed film coating, seed multilayer coating, seed encrusting, seed dripping, and seed pelleting. Specifically, the treatment is carried out by mixing the seed with the particular amount desired of seed dressing formulations either as such or after prior dilution with water in an apparatus suitable for this purpose, for example a mixing apparatus for solid or solid/liquid mixing partners, until the composition is distributed uniformly on the seed. If appropriate, this is followed by a drying operation.

Treatment of the propagules is in general only suitable for seasonal, in particular annual plants, i.e. for plants which are completely harvested after one season and which have to be replanted for the next season.

For treating the locus where the plant is growing or intended to grow, especially the soil, the latter may be treated by applying to the soil before the propagule is planted/sowed, at the time of planting or sowing along with the propagule (in case of seed sowing this is called in-furrow application), after planting/sowing or even after germination of the plant with a suitable amount of the composition of the invention either as such or after prior dilution with water.

Soil application is for example a suitable method for cereals, cotton, sunflower and trees, in particular if growing in a plantation.

In case the plants or (overground) parts thereof are to be treated, this is preferably done by spraying the plant or parts thereof, preferably their leaves (foliar application). Here, application can be carried out, for example, by customary spray techniques using spray liquor amounts of from about 100 to 1000 l/ha (for example from 300 to 400 l/ha) using water as carrier. Application of the composition of the invention by the low-volume and ultra-low-volume method is possible, as is their application in the form of microgranules.

In case of foliar treatment, the plants are treated after emergence of the plant. The optimum time for treatment depends on the specific plant species and can easily be determined by appropriate tests.

In one preferred embodiment, in the methods of the present invention, the propagules of the plants, in particular the seeds, or the soil where the plants grow or are intended to grow are treated with the composition of the invention and more preferably with component (B). If the soil is treated, this is preferably carried out as in-furrow application. Seed treatment is preferably carried out by the methods described above.

More preferably, in the methods of the present invention, the propagules of the plants, in particular the seeds, are treated with the composition of the invention and more preferably with component (B).

It was surprisingly found that the simultaneous, that means conjoint or separate, use of at least one compound listed for component (A) together with at least one compound listed for component (B) and optionally together with at least one compound listed for component (C) or—preferably—the subsequent use of components (A) and (B), more preferably in the order (B) (preferably applied for treating the propagules) and then (A), optionally in combination with (C) (preferably applied to the plant after emergence e.g. by foliar treatment) leads to a synergistic effect as regards at least one positive effect on plant health for at least one plant: The effectiveness of the composition is overadditive, i.e. it is higher than would have been expected. For instance, synergistic yield increasing effects and/or synergistic vigor improving effects can be obtained. By simultaneous application of the components (A) with a component (B) and optionally (C) together or by separate application of components (A) and (B) and optionally (C), said effects are increased more than additively. Component (A) and component (B) and the optional component (C) are thus preferably applied in synergistic amounts.

It has to be emphasized that the above effects of the composition of the invention, i.e. enhanced health of the plant, also are present when the plant is not under biotic stress and in particular when the plant is not under fungal or pest pressure. It is evident that a plant suffering from fungal or insecticidal attack produces a smaller biomass and a smaller crop yield as compared to a plant which has been subjected to curative or preventive treatment against the pathogenic fungus or pest and which can grow without the damage caused by the biotic stress factor. However, the method according to the invention leads to an enhanced plant health even in the absence of any biotic stress and in particular of any phytopathogenic fungi or pest. This means that the positive effects of the composition of the invention cannot be explained just by the fungicidal or insecticidal activities of the compounds of components (A) and (B), but are based on further activity profiles. But of course, plants under biotic stress can be treated, too, according to the methods of the present invention.

EXAMPLES

1. Yield

Soybean seeds of the soybean cultivar BRS Conquista were either left untreated or were treated either with fipronil or with thiamethoxam or with imidacloprid by means of a HEGE11 seed treatment apparatus. The seeds were sown on the very same day and cultivated under customary conditions at the University of Sao Paolo in Piracicaba County, State of Sao Paolo (Brazil) in 2006/2007. When the plants were in the growing stage $R_{1/2}$ (according to "Pocket Guide to Crop Development"; Dawn Nordby, University of Illinois Extension; beginning bloom—full bloom; corresponds approximately to growing stages 60-65 BBCH extended scale), they were treated with pyraclostrobin and epoxiconazole (in the form of the commercially available product Opera® from BASF containing 133 g/l of pyraclostrobin and 50 g/l of epoxiconazole); by spraying about 150 l/ha. The treatment was repeated when the plants were at the growing stage $R_{5.1}$ (beginning seed; seed 0.3 cm long inside pod at one of 4 uppermost nodes; pod number set; seed number determined). The plants were harvested and the grain yield was determined. The results are compiled in the table below.

TABLE 1

| No. | Treatment | Yield [kg/ha] |
|---|---|---|
| 1 | pyraclostrobin + epoxiconazole | 3337 |
| 2 | fipronil + pyraclostrobin + epoxiconazole | 3537 |
| 3 | thiamethoxam + pyraclostrobin + epoxiconazole | 3431 |
| 4 | imidacloprid + pyraclostrobin + epoxiconazole | 3509 | a.s. = active substance

The above values are the mean results of 4 replications of the experiment

2. Dry Root Mass

Seeds of the variety "BRS Conquista" were treated as in example 1. 21 days after emergence, the plants were harvested and the roots were dried and weighed. The results are shown in the table below.

TABLE 2

| No. | Treatment | Root dry mass [g/plant] |
|---|---|---|
| 1 | pyraclostrobin + epoxiconazole | 1.78 |
| 2 | fipronil + pyraclostrobin + epoxiconazole | 2.13 |
| 3 | thiamethoxam + pyraclostrobin + epoxiconazole | 2.13 |
| 4 | imidacloprid + pyraclostrobin + epoxiconazole | 2.13 | a.s. = active substance

The above values are the mean results of 4 replications of the experiment

3. Total Root Mass

Seeds of the variety "BRS Conquista" were treated as in example 1. 21 days after emergence, the plants were harvested, dried and weighed. The results are shown in the table below.

TABLE 3

| No. | Treatment | Total dry mass [g/plant] |
|---|---|---|
| 1 | pyraclostrobin + epoxiconazole | 21.92 |
| 2 | fipronil + pyraclostrobin + epoxiconazole | 23.40 |
| 3 | thiamethoxam + pyraclostrobin + epoxiconazole | 23.40 |
| 4 | imidacloprid + pyraclostrobin + epoxiconazole | 23.40 | a.s. = active substance

The above values are the mean results of 4 replications of the experiment

We claim:

1. A method for increasing the yield and/or improving the vigor of an agricultural plant, which method comprises applying fipronil at an application rate of 1 to 100 g/100 kg of seed to the seeds from which the plant is to grow, and applying pyraclostrobin at an application rate of from 0.01 to 1 kg/ha once or several times to the plant when it is in growth stage BBCH 09 to 49 or during inflorescence or flowering, wherein the agricultural plant is selected from the group consisting of soybean, corn (maize), wheat, triticale, barley, oats, rye, millet (sorghum), rice, elephant grass (Miscanthus), grass and sugar cane.

2. The method as claimed in claim 1, wherein the agricultural plant is transgenic or non-transgenic soybean.

3. The method as claimed in claim 1, wherein the agricultural plant is a non-transgenic plant or has at least one transgenic event.

4. The method as claimed in claim 1, wherein the agricultural plant is selected from the group consisting of soybean, corn (maize), wheat, triticale, barley, oats, rye, millet (sorghum) and rice.

5. The method as claimed in claim 1, wherein the agricultural plant is selected from the group consisting of soybean and corn (maize).

* * * * *